US011517343B2

(12) United States Patent
Yoshimine

(10) Patent No.: US 11,517,343 B2
(45) Date of Patent: Dec. 6, 2022

(54) VIBRATION TRANSMITTER, ULTRASONIC TRANSDUCER STRUCTURE, AND MEDICAL DEVICE

(71) Applicant: OLYMPUS CORPORATION, Hachioji (JP)

(72) Inventor: Hideto Yoshimine, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 897 days.

(21) Appl. No.: 16/383,766

(22) Filed: Apr. 15, 2019

(65) Prior Publication Data

US 2019/0239916 A1    Aug. 8, 2019

Related U.S. Application Data

(63) Continuation of application No. PCT/JP2016/080569, filed on Oct. 14, 2016.

(51) Int. Cl.
*A61B 17/32* (2006.01)
*A61B 17/29* (2006.01)
(Continued)

(52) U.S. Cl.
CPC ...... *A61B 17/320068* (2013.01); *A61B 17/29* (2013.01); *A61B 18/00* (2013.01);
(Continued)

(58) Field of Classification Search
CPC . A61B 17/320068; A61B 17/29; A61B 18/00; A61B 2017/00473;
(Continued)

(56) References Cited

U.S. PATENT DOCUMENTS 8,486,096 B2    7/2013  Robertson et al.
8,961,547 B2    2/2015  Dietz et al.
(Continued)

FOREIGN PATENT DOCUMENTS

JP    2010-051779 A    3/2010
JP    2013-519434 A    5/2013
(Continued)

OTHER PUBLICATIONS

Jan. 10, 2017 Search Report issued in International Patent Application No. PCT/JP2016/080569, 5 pages.

*Primary Examiner* — Ryan J. Severson
*Assistant Examiner* — Andrew P. Restaino
(74) *Attorney, Agent, or Firm* — Oliff PLC

(57) ABSTRACT

A vibration transmitter includes: a proximal end extending portion; a supported portion; a distal end extending portion; a first relay unit provided between the supported portion and the proximal end extending portion; and a second relay unit provided between the supported portion and the distal end extending portion. The second relay unit includes a horn that is constructed such that an outer diameter at a position continuously adjacent to the supported portion is larger than: (i) an outer diameter of the first relay unit at a position continuously adjacent to the supported portion, and (ii) the outer diameter of the distal end extending portion. The horn expands amplitude of vibration output from a distal end of
(Continued)

the distal end extending portion to be larger than a maximum amplitude at an antinode of vibration in the first relay unit or the proximal end extending portion.

18 Claims, 10 Drawing Sheets

(51) Int. Cl.
    *A61B 17/00* (2006.01)
    *H04R 17/10* (2006.01)
    *A61B 18/00* (2006.01)

(52) U.S. Cl.
    CPC .... *H04R 17/10* (2013.01); *A61B 2017/00473* (2013.01); *A61B 2017/2929* (2013.01); *A61B 2017/32009* (2017.08); *A61B 2017/320089* (2017.08)

(58) Field of Classification Search
    CPC ........... A61B 2017/2929; A61B 2017/320089; A61B 2017/32009; H04R 17/10
    See application file for complete search history.

(56) References Cited

U.S. PATENT DOCUMENTS

| | | | |
|---|---|---|---|
| 8,974,477 | B2 | 3/2015 | Yamada |
| 9,107,689 | B2 | 8/2015 | Robertson et al. |
| 9,848,901 | B2 | 12/2017 | Robertson et al. |
| 9,993,665 | B2 | 6/2018 | Sanai et al. |
| 2010/0057117 | A1 | 3/2010 | Yamada |
| 2011/0196402 | A1* | 8/2011 | Robertson .............. A61N 7/022 606/169 |
| 2011/0196404 | A1 | 8/2011 | Dietz et al. |
| 2017/0311976 | A1 | 11/2017 | Yamada et al. |
| 2018/0199957 | A1 | 7/2018 | Robertson et al. |

FOREIGN PATENT DOCUMENTS

| | | |
|---|---|---|
| JP | 2013-519440 A | 5/2013 |
| JP | 2016-022136 A | 2/2016 |
| JP | 5933874 B1 | 6/2016 |
| WO | 2011/100313 A1 | 8/2011 |
| WO | 2011/100335 A1 | 8/2011 |
| WO | 2016/035380 A1 | 3/2016 |
| WO | 2016/114290 A1 | 7/2016 |

* cited by examiner

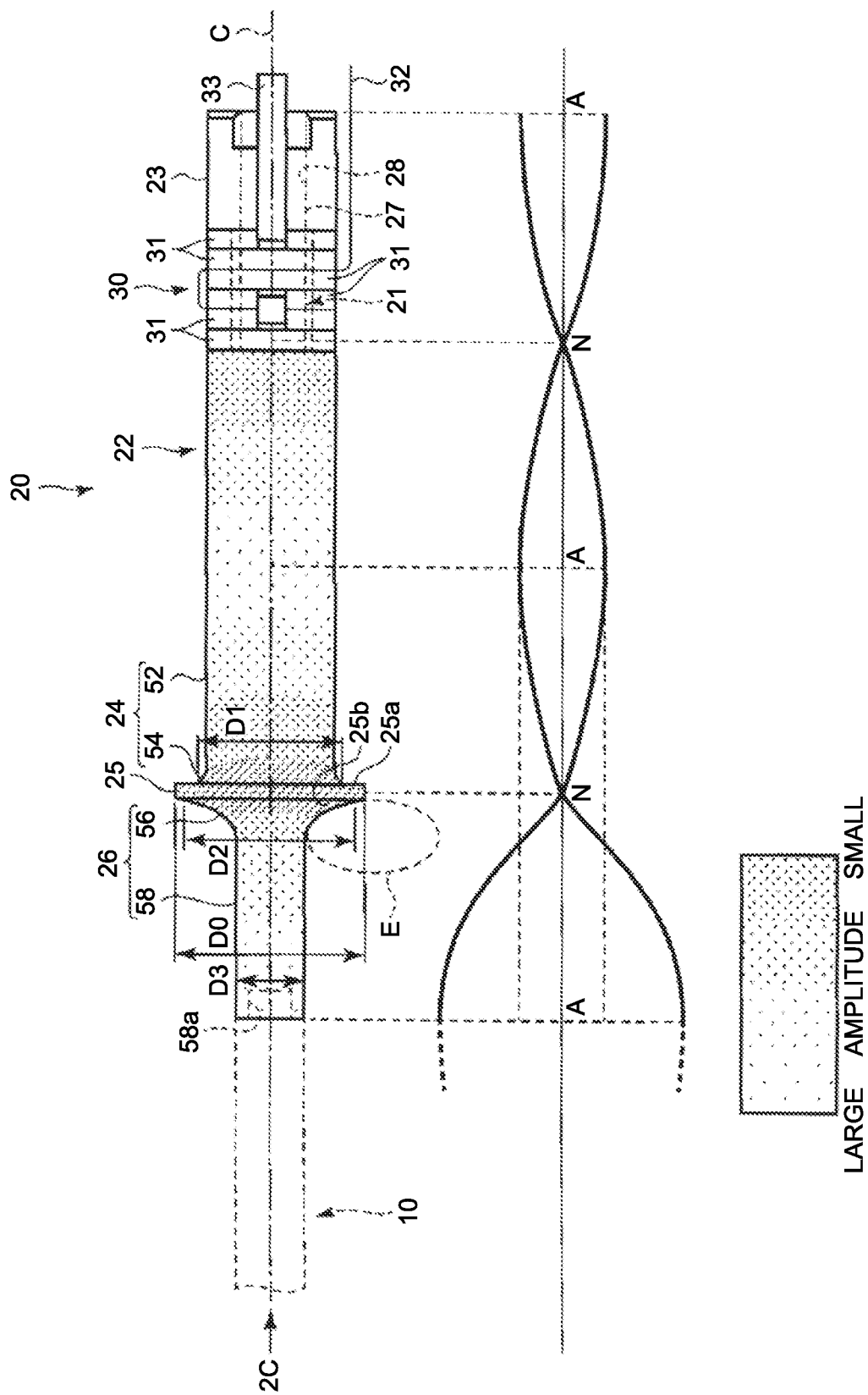

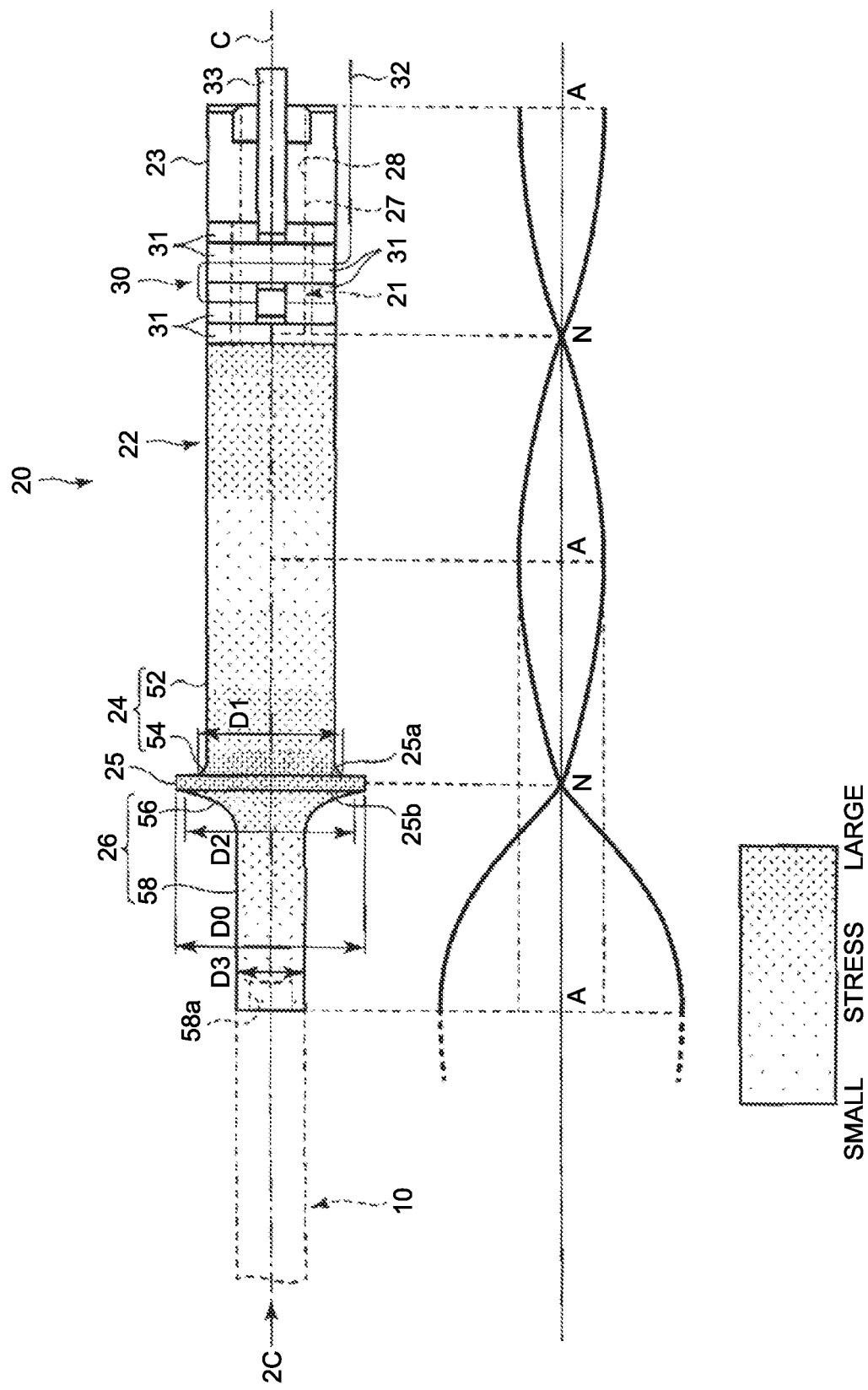

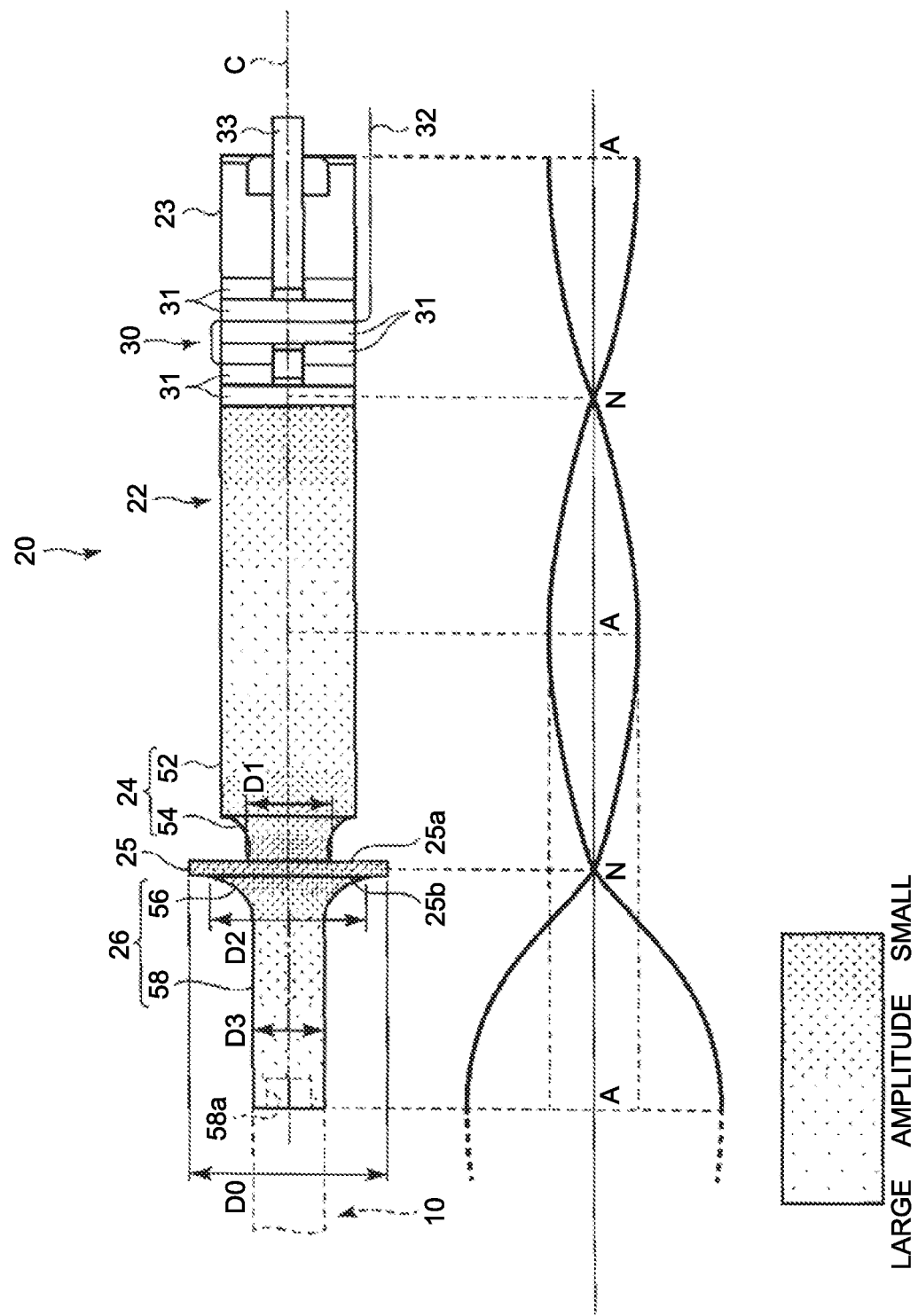

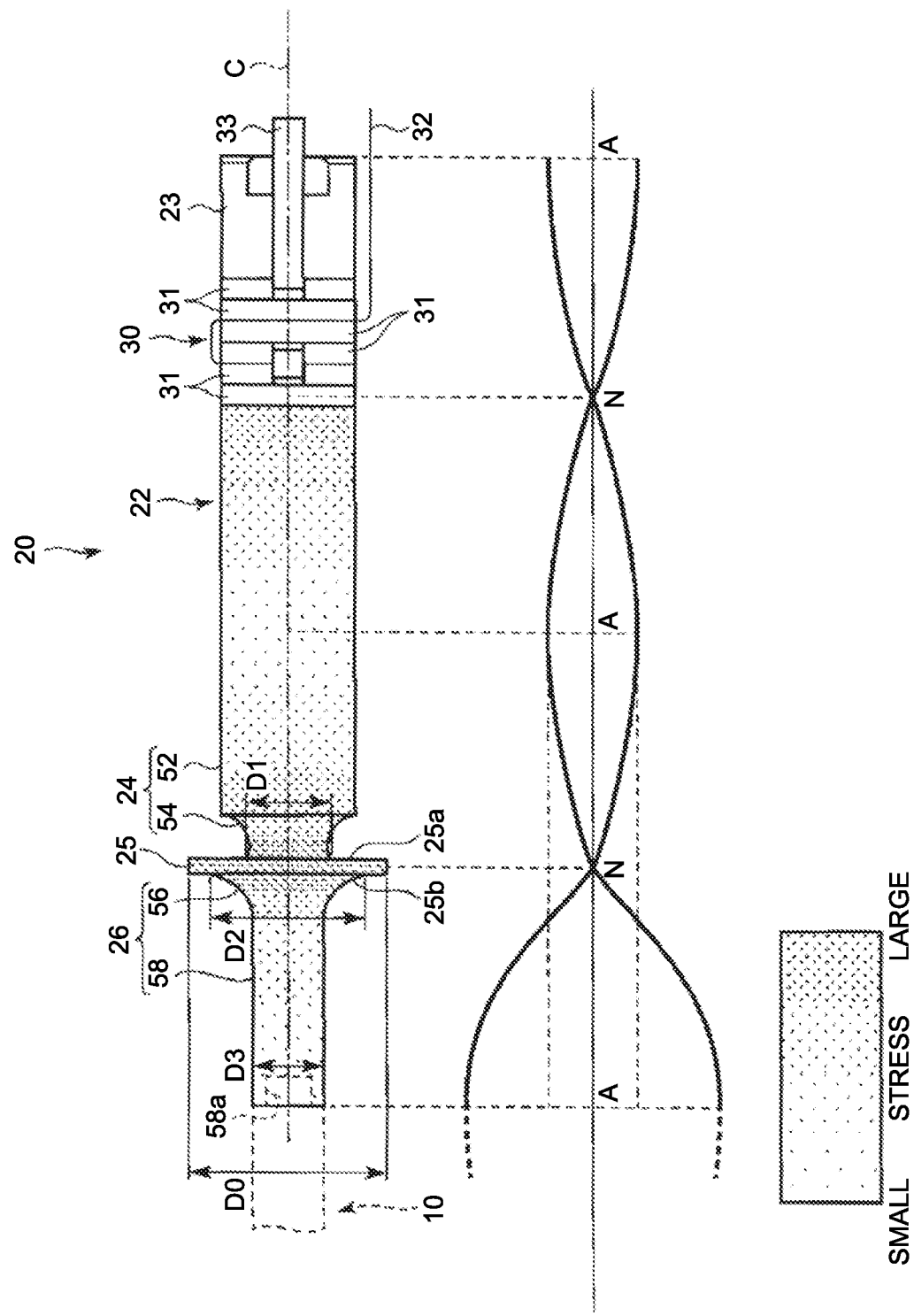

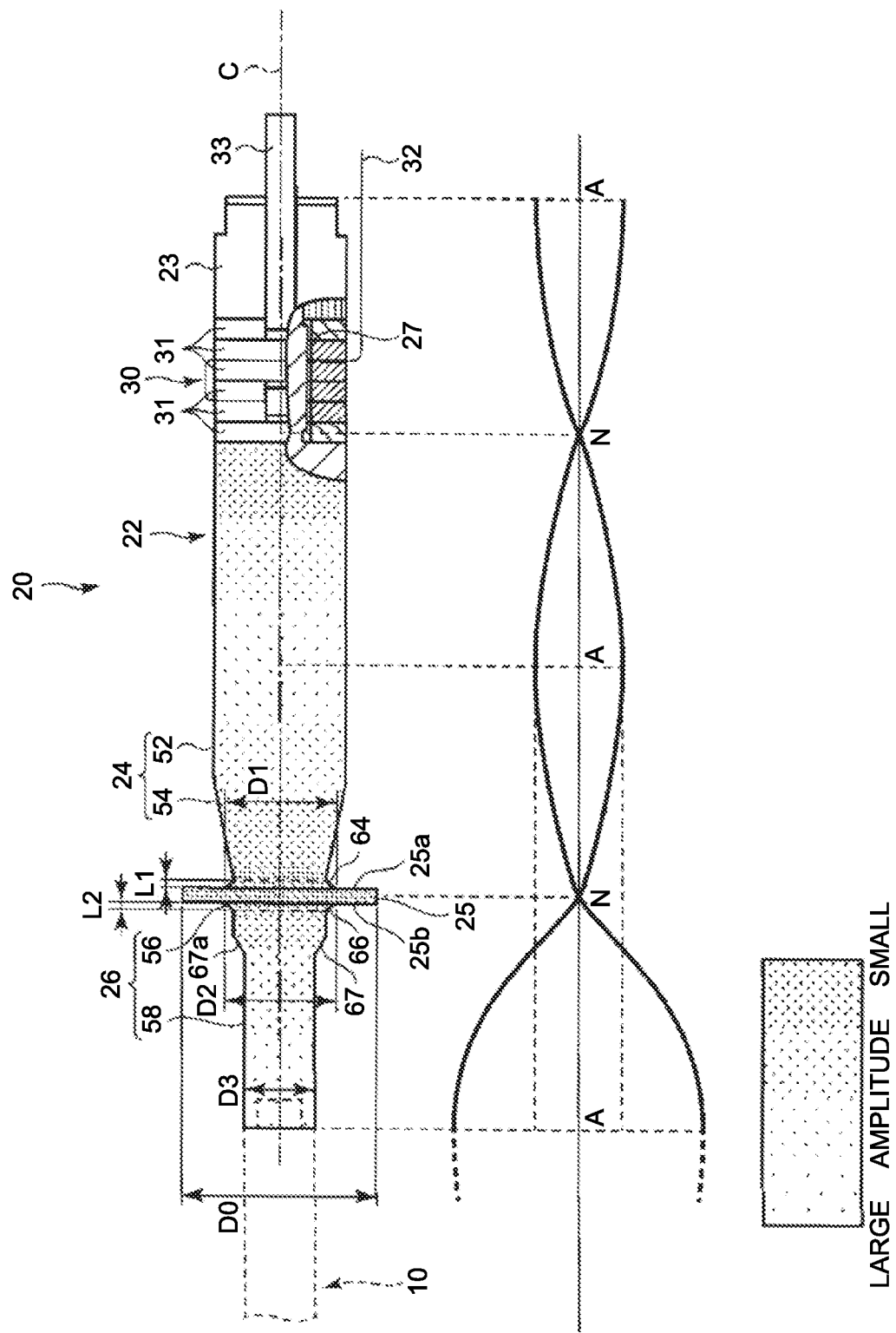

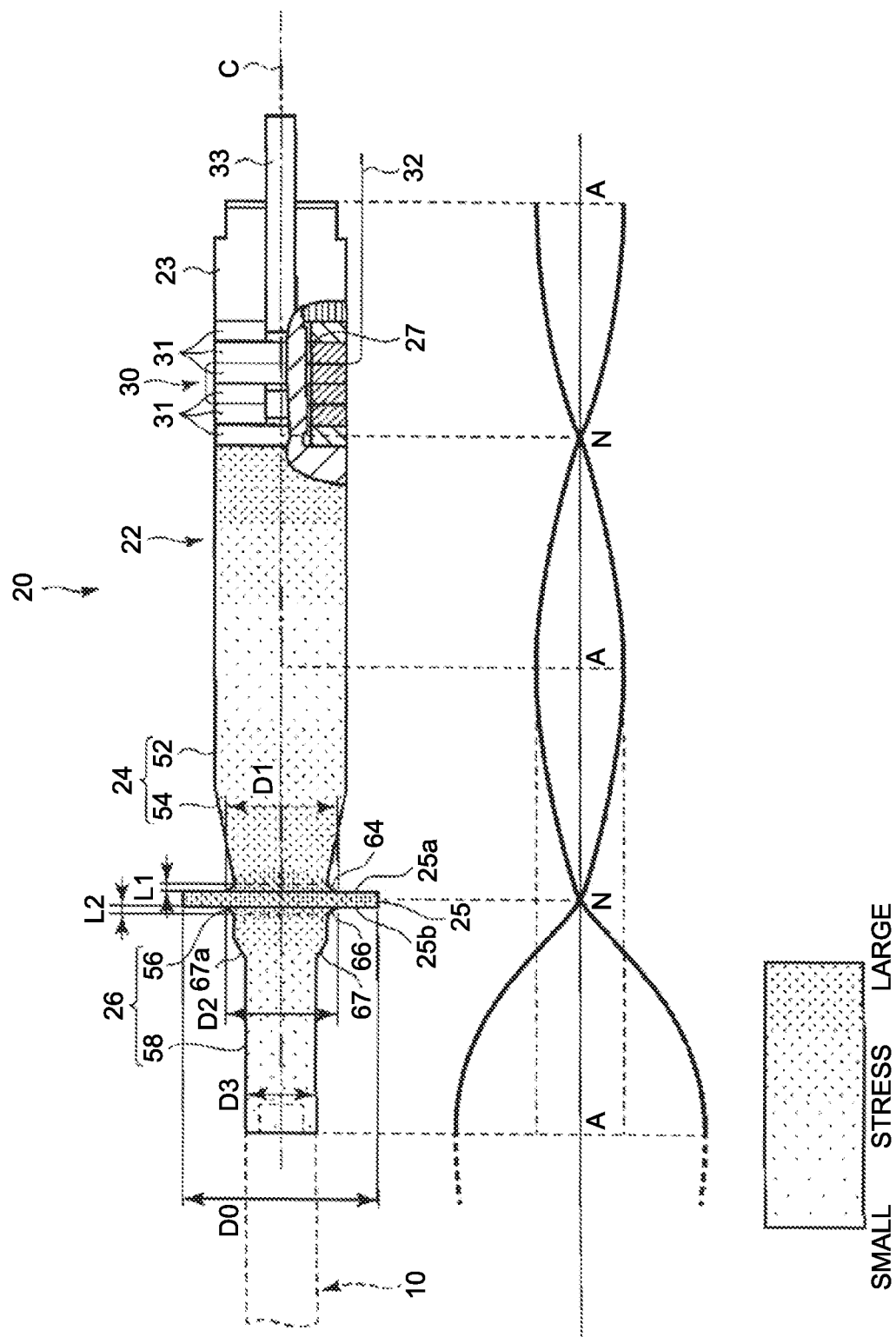

VIBRATION TRANSMITTER, ULTRASONIC TRANSDUCER STRUCTURE, AND MEDICAL DEVICE

This application is a continuation of International Application No. PCT/JP2016/080569, filed on Oct. 14, 2016, the entire contents of which are incorporated herein by reference.

BACKGROUND

The present disclosure relates to a vibration transmitter to which ultrasonic vibration is transmitted, an ultrasonic transducer structure, and a medical device.

For example, JP 2016-022136 A discloses an ultrasonic transducer structure to which longitudinal vibration of ultrasonic vibration that is generated by an ultrasonic vibrator is transmitted along a central axis. While the longitudinal vibration is being transmitted to a vibration transmitter that serves as a distal end block of the ultrasonic transducer structure, antinodes and nodes of the vibration are formed in the vibration transmitter. The vibration transmitter includes a flange-shaped supported portion that protrudes outward in a radial direction with respect to the central axis and that is supported by a housing. In the vibration transmitter, at a position corresponding to the node of the vibration in the supported portion, the sum of forces is balanced along the central axis near a region connected to a distal end side of the supported portion and a region connected to a proximal end side of the supported portion. In other words, amplitude at the node of the vibration is 0 (zero) and stable along the central axis. It is preferable that the supported portion does not transmit displacement due to the vibration to the housing; therefore, the supported portion is formed on the outer side in the radial direction at the position of the node of the vibration or in the vicinity of the node the vibration.

Here, for example, in the vicinity of the supported portion of the vibration transmitter described in JP 2016-022136 A, an outer diameter and a cross-sectional area of a proximal end portion connected to the supported portion are larger than those of a distal end portion connected to the supported portion. Therefore, in the vicinity of the supported portion distant from the central axis in the radial direction, the distal end portion has lower rigidity and is likely to be deformed, as compared to the proximal end portion. As described above, equilibrium of forces between the distal end region and the proximal end region connected to the position of the node of the vibration along the central axis are ensured, but stress distributions in the supported portion distant from the central axis in the radial direction are different between the distal end portion and the proximal end portion along the central axis in the vicinity of the supported portion. Therefore, while the longitudinal vibration is being transmitted to the vibration transmitter, a moment occurs in the supported portion due to the difference between the stress distributions, and the supported portion may be displaced.

SUMMARY

According to one aspect of the present disclosure, there is provided a vibration transmitter including: a proximal end extending portion that extends along a central axis, has a proximal end on which an ultrasonic vibrator is fixed, and receives longitudinal vibration of ultrasonic vibration generated by the ultrasonic vibrator; a supported portion that is provided on a distal end side of the proximal end extending portion along the central axis, located on an outer periphery of a node of vibration on the central axis or on an outer periphery near the node of the vibration while the longitudinal vibration is being transmitted along the central axis, protrudes outward in a radial direction with respect to the central axis, and is supported by a housing; a distal end extending portion that extends to a distal end side relative to the supported portion along the central axis, receives the longitudinal vibration of the ultrasonic vibration input to the proximal end extending portion along the central axis, and has an outer diameter smaller than an outer diameter of the supported portion; a first relay unit that is provided between the supported portion and the proximal end extending portion; and a second relay unit that is provided between the supported portion and the distal end extending portion, wherein the second relay unit includes a horn that is constructed such that an outer diameter at a position continuously adjacent to the supported portion is larger than an outer diameter of the first relay unit at a position continuously adjacent to the supported portion and larger than the outer diameter of the distal end extending portion, and that expands amplitude that is output from a distal end of the distal end extending portion with respect to maximum amplitude at an antinode of vibration in the first relay unit or the proximal end extending portion while the longitudinal vibration is being transmitted.

According to another aspect of the present disclosure, there is provided a vibration transmitter including: a proximal end extending portion that extends along a central axis, has a proximal end on which an ultrasonic vibrator is fixed, and receives longitudinal vibration of ultrasonic vibration generated by the ultrasonic vibrator; a supported portion that is provided on a distal end side of the proximal end extending portion along the central axis, located on an outer periphery of a node of vibration on the central axis or on an outer periphery near the node of the vibration while the longitudinal vibration is being transmitted along the central axis, protrudes outward in a radial direction with respect to the central axis, and is supported by a housing; a distal end extending portion that extends to a distal end side relative to the supported portion along the central axis, receives the longitudinal vibration of the ultrasonic vibration input to the proximal end extending portion along the central axis, and has an outer diameter smaller than an outer diameter of the supported portion; a first relay unit that is provided between the supported portion and the proximal end extending portion; and a second relay unit that is provided between the supported portion and the distal end extending portion, and has a certain shape by which, while the longitudinal vibration of the ultrasonic vibration is being input, stress distributions in the first relay unit at positions distant from the central axis in the radial direction become symmetric with respect to the supported portion along the central axis, and occurrence of moments in the supported portion is prevented to thereby prevent vibration of the supported portion.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2A is a schematic diagram illustrating an ultrasonic transducer structure of a treatment tool of a treatment system according to an exemplary embodiment, and schematically illustrating antinodes, nodes, and amplitude of vibration in a case where a driving unit of the ultrasonic transducer structure generates ultrasonic vibration and inputs longitudinal vibration of the ultrasonic vibration to a vibration transmitter;

FIG. 2B is a schematic diagram illustrating the ultrasonic transducer structure of the treatment tool of the treatment system according to an exemplary embodiment, and schematically illustrating antinodes, nodes, and amplitude of vibration and a stress distribution in the vibration transmitter in a case where the driving unit of the ultrasonic transducer structure generates ultrasonic vibration and inputs longitudinal vibration of the ultrasonic vibration to the vibration transmitter;

FIG. 4A is a schematic diagram illustrating an ultrasonic transducer structure of a treatment tool of a treatment system according to an exemplary embodiment, and schematically illustrating antinodes, nodes, and amplitude of vibration in a case where a driving unit of the ultrasonic transducer structure generates ultrasonic vibration and inputs longitudinal vibration of the ultrasonic vibration to a vibration transmitter;

FIG. 4B is a schematic diagram illustrating the ultrasonic transducer structure of the treatment tool of the treatment system according to an exemplary embodiment, and schematically illustrating antinodes, nodes, and amplitude of vibration and a stress distribution in the vibration transmitter in a case where the driving unit of the ultrasonic transducer structure generates ultrasonic vibration and inputs longitudinal vibration of the ultrasonic vibration to the vibration transmitter;

FIG. 5A is a schematic diagram illustrating an ultrasonic transducer structure of a treatment tool of a treatment system according to an exemplary embodiment, and schematically illustrating antinodes, nodes, and amplitude of vibration in a case where a driving unit of the ultrasonic transducer structure generates ultrasonic vibration and inputs longitudinal vibration of the ultrasonic vibration to a vibration transmitter; and FIG. 5B is a schematic diagram illustrating the ultrasonic transducer structure of the treatment tool of the treatment system according to an exemplary embodiment, and schematically illustrating antinodes, nodes, and amplitude of vibration and a stress distribution in the vibration transmitter in a case where the driving unit of the ultrasonic transducer structure generates ultrasonic vibration and inputs longitudinal vibration of the ultrasonic vibration to the vibration transmitter.

DETAILED DESCRIPTION

Modes for carrying out the present disclosure will be described below with reference to the drawings.

An exemplary embodiment will be described with reference to FIG. 1 to FIG. 3B.

Figure 1:
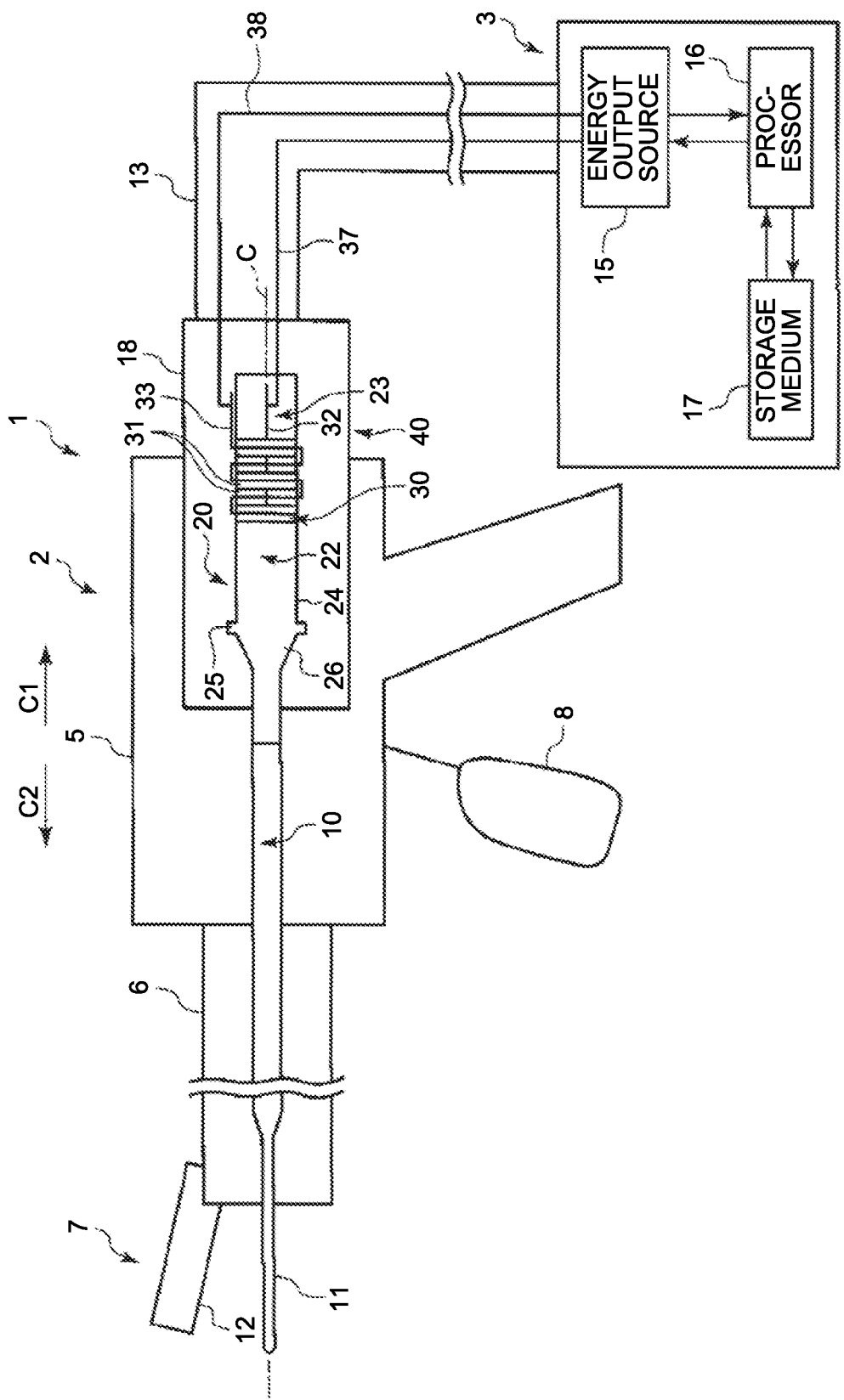
FIG. 1 is a schematic diagram illustrating a treatment system according to exemplary embodiments.

FIG. 1 illustrates a treatment system 1 in which an ultrasonic transducer structure 20 of an exemplary embodiment is used. As illustrated in FIG. 1, the treatment system 1 includes an ultrasonic treatment tool (medical device) 2 and an energy control device 3. The ultrasonic treatment tool 2 includes a housing (base housing) 5 that can be held by a user, and a shaft (hard pipe) 6 attached to the housing 5. The shaft 6 is extended in an approximately straight manner. Here, in the ultrasonic treatment tool 2, a side on which the housing 5 is located relative to the shaft 6 is referred to as a proximal end side (an arrow C1 side), and a side opposite to the proximal end side is referred to as a distal end side (an arrow C2 side). Therefore, the shaft 6 is attached to the housing 5 from the distal end side. Further, the ultrasonic treatment tool 2 includes an end effector 7 in a region on the distal end side of the shaft 6.

A handle 8 is rotatably attached to the housing 5. The housing 5 and the handle 8 are made of, for example, a plastic material having electrical insulation property. The handle 8 is opened or closed with respect to the housing 5 by being rotated with respect to the housing 5. Further, a rod-like member (vibration transmitting member) 10 is inserted in the shaft 6. The rod-like member 10 is made of a material, such as titanium alloy, that has high vibration transmissibility. The rod-like member 10 is extended toward the distal end side from the inside of the housing 5 through the inside of the shaft 6. In addition, the rod-like member 10 includes a rod protruding portion (treatment unit) 11 that protrudes from a distal end of the shaft 6 toward the distal end side. Furthermore, a jaw 12 is rotatably attached to a distal end portion of the shaft 6. The jaw 12 and the handle 8 are connected via a movable member (not illustrated) that is extended through the inside of the shaft 6. The movable member moves to the proximal end side or the distal end side by opening or closing the handle 8 with respect to the housing 5. Accordingly, the jaw 12 rotates with respect to the shaft 6, and a space between the jaw 12 and the rod protruding portion 11 is opened or closed. In this embodiment, the end effector 7 is constructed by the rod protruding portion 11 and the jaw 12. A treatment target, such as body tissue, is treated by holding the treatment target between the jaw 12 and the rod protruding portion 11.

Meanwhile, in some embodiments, a rotation knob (not illustrated) that is a rotation operating member is attached to the housing 5. The rotation knob is rotatable about a central axis of the shaft 6 relative to the housing 5. In this case, by rotating the rotation knob, the shaft 6, the end effector 7, and the rod-like member 10 rotate together about the central axis of the shaft 6 relative to the housing 5. Furthermore, in some other embodiments, the jaw 12 is not provided and the end effector 7 is constructed by only the rod protruding portion 11. In this case, the handle 8 and the movable member as described above are not provided. Moreover, in this case, the rod protruding portion 11 has a hook shape, a paddle shape, a blade shape, or the like.

The ultrasonic transducer structure 20 is connected to the rod-like member 10 from the proximal end side inside the housing 5. In this embodiment, the ultrasonic transducer structure 20 is housed inside a transducer housing (transducer case) 18 that has electrical insulation property, and supported by the transducer housing 18. It is preferable to handle the transducer housing 18 and the ultrasonic transducer structure 20 as an integrated medical device 40. Meanwhile, it is preferable that the medical device 40 includes a cable 13. By attaching the transducer housing 18 to the housing 5 from the proximal end side, a distal end of the ultrasonic transducer structure 20 is connected to a proximal end of the rod-like member 10. In this embodiment, the distal end of the ultrasonic transducer structure 20 is directly connected to the proximal end of the rod-like member 10. Furthermore, in this embodiment, one end of the cable 13 is connected to the transducer housing 18. The other end of the cable 13 is removably connected to the energy control device 3.

Meanwhile, in some other embodiments, the transducer housing 18 is not provided. In this case, the ultrasonic transducer structure 20 is supported by the housing 5 and one end of the cable 13 is connected to the housing 5. Further, in the embodiments in which the rotation knob is provided as described above, by rotating the rotation knob, the ultrasonic transducer structure 20 rotates together with the shaft 6, the end effector 7, and the rod-like member 10 about the central axis of the shaft 6 relative to the housing 5.

Figure 2C:
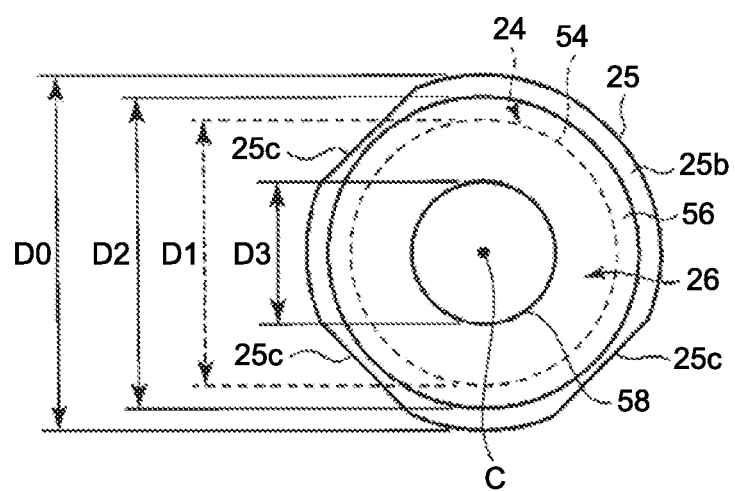
FIG. 2C is a schematic diagram illustrating the ultrasonic transducer structure viewed in a direction indicated by an arrow 2C in FIG. 2A and FIG. 2B.

FIG. 2A and FIG. 2B illustrate the ultrasonic transducer structure 20. FIG. 2C illustrates a vibration transmitter 22 viewed in a direction indicated by an arrow 2C in FIG. 2A and FIG. 2B.

As illustrated in FIG. 2A and FIG. 2B, the ultrasonic transducer structure 20 includes the vibration transmitter (distal end block) 22, an ultrasonic vibrator 30, and a pressing body (proximal end block) 23. The ultrasonic transducer structure 20 includes a bolt (shaft) 21 that has a central axis C serving as a central axis thereof. Here, one end side in a direction along the central axis C corresponds to the proximal end side (arrow C1 side), and the other end side in the direction along the central axis C corresponds to the distal end side (arrow C2 side). The bolt 21 is extended from the proximal end to the distal end in a straight manner along the central axis C.

As illustrated in FIG. 2A, in the ultrasonic transducer structure 20, a distal end portion of the bolt 21 is connected to the vibration transmitter (distal end block) 22 that serves as a front mass. In this embodiment, the vibration transmitter 22 is integrated with the bolt 21. The vibration transmitter 22 and the bolt 21 are made of, for example, titanium alloy, aluminum alloy, stainless steel (SUS), or the like. In particular, it is preferable that the vibration transmitter 22 and the bolt 21 are made of titanium alloy. Meanwhile, the vibration transmitter 22 may be made of the same material as the bolt 21 or may be made of a different material from the bolt 21.

In the ultrasonic transducer structure 20, a proximal end portion of the bolt 21 is connected to the pressing body (proximal end block) 23 that serves as a back mass. In this embodiment, the pressing body 23 is formed in a ring shape so as to cover an outer periphery of the bolt 21. A male screw portion 27 serving as a first engaging unit is formed on the outer periphery of the proximal end portion of the bolt 21. Further, a female screw portion 28 serving as a second engaging unit that engages with the first engaging unit is formed on an inner periphery of the pressing body 23. In this embodiment, the male screw portion 27 is extended from the proximal end to the distal end side of the bolt 21, and the female screw portion 28 is extended from the proximal end to the distal end side of the pressing body 23. When the male screw portion 27 and the female screw portion 28 are engaged with each other, i.e., screwed together, the pressing body 23 is fastened onto the outer periphery of the bolt 21. Therefore, in this embodiment, the pressing body 23 serves as a fastener member that is fastened onto the outer periphery of the bolt 21.

The pressing body 23 is made of, for example, titanium alloy, aluminum alloy, SUS, or the like. Here, the pressing body 23 may be made of the same material as the vibration transmitter 22 or may be made of a different material from the vibration transmitter 22.

The ultrasonic vibrator (piezoelectric element group) 30 serving as a driving unit that generates ultrasonic vibration is mounted on the outer periphery of the the bolt 21. The ultrasonic vibrator 30 is sandwiched between the vibration transmitter 22 and the pressing body 23 in the direction along the central axis C. Further, the ultrasonic vibrator 30 is pressed toward the distal end side by the pressing body 23. In this embodiment, the ultrasonic vibrator 30 includes a plurality of piezoelectric elements 31. For example, the piezoelectric elements 31 are made of a material, such as ceramics, that have different material quality (physical property value), such as modulus of rigidity, from that of the bolt 21. The piezoelectric elements 31 convert electrical energy into vibration. Each of the piezoelectric elements 31 is formed in a ring shape, and the bolt 21 is inserted in each of the piezoelectric elements 31. Meanwhile, it is sufficient to provide at least the single piezoelectric element 31.

The ultrasonic vibrator 30 includes a plurality of ring-shaped electrode members 32 that are made of an electrical conductive material, such as metal, and connected to one another, and includes a plurality of ring-shaped electrode members 33 that are made of an electrical conductive material, such as metal, and connected to one another. One end of an electrical wiring 37 is connected to the electrode members 32. Further, one end of an electrical wiring 38 is connected to the electrode members 33. Meanwhile, the numbers of the electrode members 32 and 33 are determined in accordance with the number of the piezoelectric elements 31, and in any case, each of the piezoelectric elements 31 is sandwiched between a corresponding one of the electrode members 32 and a corresponding one of the electrode members 33.

Insulators are provided between a distal end of the ultrasonic vibrator 30 and a proximal end of the vibration transmitter 22 and between a proximal end of the ultrasonic vibrator 30 and a distal end of the pressing body 23, although they are not illustrated in the drawings. An insulating tube (not illustrated) made of an electrically insulating material is provided between an inner periphery of the ultrasonic vibrator 30 and the outer periphery of the bolt 21. With this configuration, it is possible to prevent electrical energy supplied to the ultrasonic vibrator 30 from being supplied to the vibration transmitter 22, the pressing body 23, and the bolt 21. Therefore, it is possible to prevent an electric current that occurs due to voltage applied to the ultrasonic vibrator 30 from flowing into a patient via the vibration transmitter 22 and the rod-like member 10. Further, the insulators prevent signals supplied from other devices from being input to the ultrasonic vibrator 30 via the rod-like member 10 and the vibration transmitter 22.

In an exemplary embodiment, the ultrasonic transducer structure 20 is configured as described above; therefore, the ultrasonic transducer structure 20 is a bolt-clamped Langevin-type transducer. The vibration transmitter 22 serves as the distal end of the ultrasonic transducer structure 20 and is connected to the rod-like member 10.

The energy control device 3 includes an energy output source 15, a processor 16, and a storage medium 17. The electrical wirings 37 and 38 are extended through the inside of the cable 13, and other ends of the electrical wirings 37 and 38 are connected to the energy output source 15. The energy output source 15 includes, for example, a conversion circuit that converts electric power obtained from a battery power supply or a receptacle outlet fixed on a wall into electrical energy to be supplied to the ultrasonic vibrator 30 of the ultrasonic transducer structure 20, and outputs the converted electrical energy. The electrical energy output from the energy output source 15 is supplied to the ultrasonic vibrator 30 via the electrical wirings 37 and 38. The energy output source 15 outputs alternating-current power as the electrical energy to the ultrasonic vibrator 30.

The processor 16 that serves as a control unit is constructed by an integrated circuit that includes a central processing unit (CPU), an application specific integrated circuit (ASIC), or a field programmable gate array (FPGA). The processor 16 performs processes in accordance with a program that is stored in the processor 16 or the storage medium 17. Further, the storage medium 17 stores therein a processing program used by the processor 16 and parameters, tables, and the like used for calculations by the processor 16. The processor 16 controls output of the electrical energy from the energy output source 15 to the ultrasonic vibrator 30. In an exemplary embodiment, the ultrasonic transducer structure 20 is set so as to resonate at a predetermined frequency, such as 47 kilohertz (kHz). In an exemplary embodiment, the processor 16 adjusts a frequency of output of the electrical energy from the energy output source 15 to a predetermined frequency. For example, in some embodiments, the predetermined frequency is 47 kHz.

As illustrated in FIG. 1 to FIG. 2C, the vibration transmitter 22 includes a first vibrating unit 24, a supported portion 25, and a second vibrating unit 26 in this order from the proximal end side to the distal end side along the central axis C. It is preferable that the vibration transmitter 22 is integrally formed by cutting a rod-shaped titanium alloy material, for example. Meanwhile, an outer diameter D0 of the supported portion 25 (twice a distance (radius) from the central axis C to a most distant point along a radial direction of the central axis C) is larger than an outer diameter D1 of a first relay unit 54 of the first vibrating unit 24 (to be described later) and larger than an outer diameter D2 of a second relay unit 56 of the second vibrating unit 26 (to be described later).

The first vibrating unit 24 includes a proximal end extending portion 52 and the first relay unit 54 in this order from the proximal end side to the distal end side along the central axis C. The proximal end extending portion 52 extends along the central axis C, has a proximal end on which the ultrasonic vibrator 30 is fixed by the pressing body 23, and receives longitudinal vibration of ultrasonic vibration. The first relay unit 54 is provided between the supported portion 25 and the proximal end extending portion 52. A distal end of the first relay unit 54 is connected to a proximal end surface 25a of the supported portion 25. A space between the distal end of the first relay unit 54 and the proximal end surface 25a of the supported portion 25 is formed of an appropriate curved surface that is smooth and continuous, in order to prevent stress concentration.

The second vibrating unit 26 includes the second relay unit 56 and a distal end extending portion 58 in this order from the proximal end side to the distal end side along the central axis C. The second relay unit 56 is provided between the supported portion 25 and the distal end extending portion 58. A proximal end of the second relay unit 56 is connected to a distal end surface 25b of the supported portion 25. A space between the proximal end of the second relay unit 56 and the distal end surface 25b of the supported portion 25 is formed of an appropriate curved surface that is smooth and continuous, in order to prevent stress concentration. Meanwhile, when the longitudinal vibration of the ultrasonic vibration is input to a proximal end of the proximal end extending portion 52, a distal end of the distal end extending portion 58 corresponds to an antinode A of the vibration, at which amplitude is maximum, in the vibration transmitter 22.

The distal end extending portion 58 includes, at the distal end thereof, a connecting portion 58a to which the appropriate rod-like member 10 having the rod protruding portion (treatment unit) 11 is connectable on the distal end side along the central axis C. The rod protruding portion 11 corresponds to the antinode A of the vibration when the longitudinal vibration of the ultrasonic vibration is input to the proximal end of the proximal end extending portion 52.

The supported portion 25 protrudes outward in the radial direction with respect to the central axis C, and supported by the transducer housing 18. The supported portion 25 is provided on the distal end side relative to the proximal end extending portion 52 along the central axis C and located on an outer periphery of a node N of the vibration on the central axis C or on an outer periphery near the node N of the vibration while the longitudinal vibration is being transmitted along the central axis C. The supported portion 25 is has a plate shape that protrudes outward in the radial direction with respect to the central axis C. It is preferable that the supported portion 25 has an approximately disk shape. Meanwhile, the supported portion 25 includes, at an outer edge thereof, rotation restricting units 25c that prevent rotation about the central axis C relative to the transducer housing 18. Further, the supported portion 25 is supported by the transducer housing 18. Therefore, the rotation restricting units 25c restrict rotation of the supported portion 25 about the central axis C relative to the transducer housing 18.

The second relay unit 56 is used as a horn that expands amplitude that is output from the distal end of the distal end extending portion 58 with respect to the maximum amplitude at the antinode A of the vibration in the first relay unit 54 or the proximal end extending portion 52 while the longitudinal vibration is being transmitted. A cross-sectional area of the second relay unit 56 is gradually reduced in a short distance from the proximal end side to the distal end side along the central axis C. The second relay unit 56 is connected to the distal end side of the supported portion 25 provided on an outer side of the position of the node N of the vibration or on an outer side near the position of the node N of the vibration. As will be described later, a stress becomes maximum at the node N of the vibration and near the node N of the vibration while the vibration is being transmitted to the vibration transmitter 22. Therefore, a stress becomes maximum near the supported portion 25 in the vibration transmitter 22. Therefore, a metamorphic rate of the second relay unit 56, i.e., the degree of change in the cross-sectional area, has an influence on an expansion rate of the amplitude at the distal end of the distal end extending portion 58.

Here, a cross-sectional surface that is perpendicular to the central axis C at a boundary between the second relay unit 56 and the distal end surface 25b of the supported portion 25 has a larger area than a cross-sectional surface that is perpendicular to the central axis C at a boundary between the first relay unit 54 and the proximal end surface 25a of the supported portion 25. The outer diameter D2 of the second relay unit 56 at a position continuously adjacent to the supported portion 25 is larger than the outer diameter D1 of the first relay unit 54 at a position continuously adjacent to the supported portion 25. In other words, the boundary that is provided between the second relay unit 56 and the distal end surface 25b of the supported portion 25 and defined by the maximum outer diameter D2 of the second relay unit 56 is located on the outer side in the radial direction with respect to the central axis C, relative to the boundary that is provided between the first relay unit 54 and the proximal end surface 25a of the supported portion 25 and defined by the maximum outer diameter D1 of the first relay unit 54. Therefore, in the distal end surface 25b of the supported portion 25, a thickness of the distal end surface 25b is apparently increased relative to a thickness of the proximal end surface 25a at positions distant from the central axis C in the radial direction, in order to increase rigidity of the distal end surface 25b side. Meanwhile, because the second relay unit 56 is constructed as a horn, the diameter of the second relay unit 56 is gradually reduced from the maximum outer diameter D2 from the supported portion 25 to the distal end side along the central axis C.

An outer diameter of the distal end extending portion 58 at an arbitrary position is denoted by D3 (D2). The distal end extending portion 58 extends to the distal end side relative to the second relay unit 56 along the central axis C. The outer diameter D3 of a proximal end of the distal end extending portion 58 is smaller than the outer diameter D2 of the second relay unit 56 at the boundary between the proximal end of the second relay unit 56 and the distal end surface 25b of the supported portion 25. Therefore, the outer diameter D2 of the second relay unit 56 at a position continuously adjacent to the distal end surface 25b of the supported portion 25 is larger than the outer diameter D1 of the first relay unit 54 at a position continuously adjacent to the proximal end surface 25a of the supported portion 25 and larger than the outer diameter D3 of the distal end extending portion 58. Meanwhile, the outer diameter D3 of the proximal end of the distal end extending portion 58 corresponds to the outer diameter D2 of the distal end of the second relay unit 56.

In this example, an outer peripheral surface of the second relay unit 56 has a curved surface (R-curve) formed by a part of an ellipse E (¼ ellipse) indicated by a dashed line in FIG. 2A. Here, a long axis of the ellipse E is in a direction perpendicular to the central axis C, and a short axis of the ellipse E is in a direction parallel to the central axis C. Therefore, it is possible to change the outer diameter D2 in a shorter distance than a case in which the curved surface is formed by a part of a circle (¼ circle). In other words, it is possible to match the outer diameter D2 with the outer diameter D3 in a short distance on the distal end side of the supported portion 25. Therefore, due to the shape of the second relay unit 56, it is possible to improve the amplitude expansion rate. Meanwhile, ellipticity of the ellipse E that forms the curved surface on the outer peripheral surface of the second relay unit 56 is appropriately adjusted based on a relationship with a stress distribution to be described later.

Here, an upper figure in FIG. 2A illustrates a state in which the distal end of the distal end extending portion 58 of the second vibrating unit 26 is displaced on the most proximal end side along the central axis C. A portion with high dot density in the upper figure of FIG. 2A indicates that an absolute value of the amplitude is small, and the absolute value of the amplitude is increased with a decrease in the density. Similarly to the upper figure in FIG. 2A, an upper figure in FIG. 2B illustrates a state in which the distal end of the distal end extending portion 58 of the second vibrating unit 26 is displaced on the most proximal end side along the central axis C. Dots in the upper figure of FIG. 2B indicate a stress distribution of the vibration transmitter 22 in the state in which the distal end of the distal end extending portion 58 of the second vibrating unit 26 is displaced on the most proximal end side along the central axis C. A portion with high dot density in FIG. 2B indicates that an absolute value of the stress is large, and the absolute value of the stress is reduced with a decrease in the density.

Meanwhile, titanium alloy used as the material of the vibration transmitter 22 as described above is used in an elastic region, so that a stress and a distortion are proportional to each other. Therefore, the dot density indicating the stress distribution in FIG. 2B can be regarded as indicating a distortion that occurs in the vibration transmitter 22 while the vibration is being transmitted.

Lower figures in FIG. 2A and FIG. 2B illustrate amplitude of vibration at each position of the vibration transmitter 22 along the central axis C and positions of the antinodes A and the nodes N of the vibration in a case where the ultrasonic vibrator 30 of the ultrasonic transducer structure 20 generates ultrasonic vibration and inputs longitudinal vibration of the ultrasonic vibration to the vibration transmitter 22. The amplitude in the lower figures of FIG. 2A and FIG. 2B is schematically illustrated, and, in reality, the vibration transmitter 22 is displaced along the central axis C instead of being displaced in a direction perpendicular to the central axis C. Therefore, the amplitude of the vibration transmitter 22 is displaced along the central axis C. Further, while the vibration is being transmitted to the vibration transmitter 22, the amplitude becomes minimum, i.e., 0 (zero), and the stress and the distortion become maximum at the positions corresponding to the nodes N of the vibration, and the amplitude becomes maximum and the stress and the distortion become minimum, i.e., 0 (zero), at the position corresponding to the antinodes A of the vibration.

The first relay unit 54 and the second relay unit 56 have certain shapes that are symmetric or approximately symmetric with respect to the central axis C. Therefore, in the vibration transmitter 22, at the positions corresponding to the nodes N of the vibration on the central axis C, a region of the first relay unit 54 that is connected to the proximal end side of the supported portion 25 and a region of the second relay unit 56 that is connected to the distal end side of the supported portion 25 are displaced on the opposite sides along the central axis C. In the examples illustrated in the upper figures of FIG. 2A and FIG. 2B, in the vicinity of the supported portion 25, the first relay unit 54 is displaced in a distal end direction C2 of the vibration transmitter 22 and the second relay unit 56 is displaced in a proximal end direction C1 of the vibration transmitter 22. In this case, at the position corresponding to the node N of the vibration inside the supported portion 25, the sum of forces is balanced along the central axis C.

As illustrated in the upper figure of FIG. 2B, the outer diameter D2 of the second relay unit 56 at the boundary with the distal end surface 25b of the supported portion 25 is larger than the outer diameter D1 of the first relay unit 54 at the boundary with the proximal end surface 25a of the supported portion 25. In other words, due to both of the supported portion 25 and the second relay unit 56, a thickness of the distal end surface 25b side (thickness parallel to the central axis C) at a position that is distant from the central axis C relative to the outer diameter D1 located at the boundary between the first relay unit 54 and the proximal end surface 25a of the supported portion 25 in the radial direction perpendicular to the central axis C is increased. Therefore, in the supported portion 25, rigidity of a region connected to the distal end surface 25b is larger than that of a region connected to the proximal end surface 25a.

In the vicinity of the node N of the vibration in FIG. 2B, stresses are applied in opposite directions along the central axis C. In this case, at the position corresponding to the node N of the vibration inside the supported portion 25, the sum of forces is balanced along the central axis C. In FIG. 2B, in the supported portion 25 distant from the central axis C in the radial direction and in the vicinity thereof, stress distributions of the supported portion 25 are substantially the same between the distal end side and the proximal end side of the supported portion 25 along the central axis C. The first relay unit 54 and the second relay unit 56 of the vibration transmitter 22 according to this embodiment have certain shapes by which, while the longitudinal vibration of the ultrasonic vibration is being input to the vibration transmitter 22, the stress distribution in the first relay unit 54 connected to the proximal end side of the supported portion 25 and the stress distribution in the second relay unit 56 connected to the distal end side are, at positions distant from the central axis C in the radial direction, balanced with respect to the supported portion 25 along the central axis C. In other words, moments near the proximal end surface 25a and the distal end surface 25b of the supported portion 25 distant from the central axis C in the radial direction are cancelled out due to the principle of superposition. Therefore, the stress distribution of the supported portion 25 in the upper figure of FIG. 2B indicates that it is possible to, at positions distant from the central axis C in the radial direction, counteract against a load that is applied when the distal end of the distal end extending portion 58 of the second vibrating unit 26 is displaced on the most proximal end side along the central axis C. Therefore, the first relay unit 54, the supported portion 25, and the second relay unit 56 of the vibration transmitter 22 according to this embodiment have certain shapes that prevent occurrence of moments in the supported portion 25.

Meanwhile, the rigidity near the boundary between the distal end surface 25b of the supported portion 25 and the proximal end of the second relay unit 56 is larger than the rigidity near the boundary between the proximal end surface 25a of the supported portion 25 and the distal end of the first relay unit 54. Therefore, in the examples illustrated in the upper figures of FIG. 2A and FIG. 2B, it is possible to prevent occurrence of moments in the supported portion 25 that may cause the supported portion 25 to move to the distal end side along the central axis C against the load that is applied when the distal end of the distal end extending portion 58 of the second vibrating unit 26 is displaced on the most distal end side along the central axis C.

As described above, the first relay unit 54, the supported portion 25, and the second relay unit 56 of the vibration transmitter 22 according to this embodiment have certain shapes that prevent occurrence of moments in the supported portion 25 while the longitudinal vibration of the ultrasonic vibration is being input to the vibration transmitter 22. Therefore, while the longitudinal vibration of the ultrasonic vibration is being input to the vibration transmitter 22, the first relay unit 54 and the second relay unit 56 are able to balance a displacement distribution of the first relay unit 54 and a displacement distribution of the second relay unit 56 between the distal end side and the proximal end side of the supported portion 25, not only at positions along the central axis C but also in the supported portion 25 distant from the central axis C. In this manner, by balancing the displacement distribution of the first relay unit 54 and the displacement distribution of the second relay unit 56 not only at positions along the central axis C but also at positions distant from the central axis C, the first relay unit 54 and the second relay unit 56 prevent displacement of the supported portion 25, in cooperation with the supported portion 25.

Figure 3A:
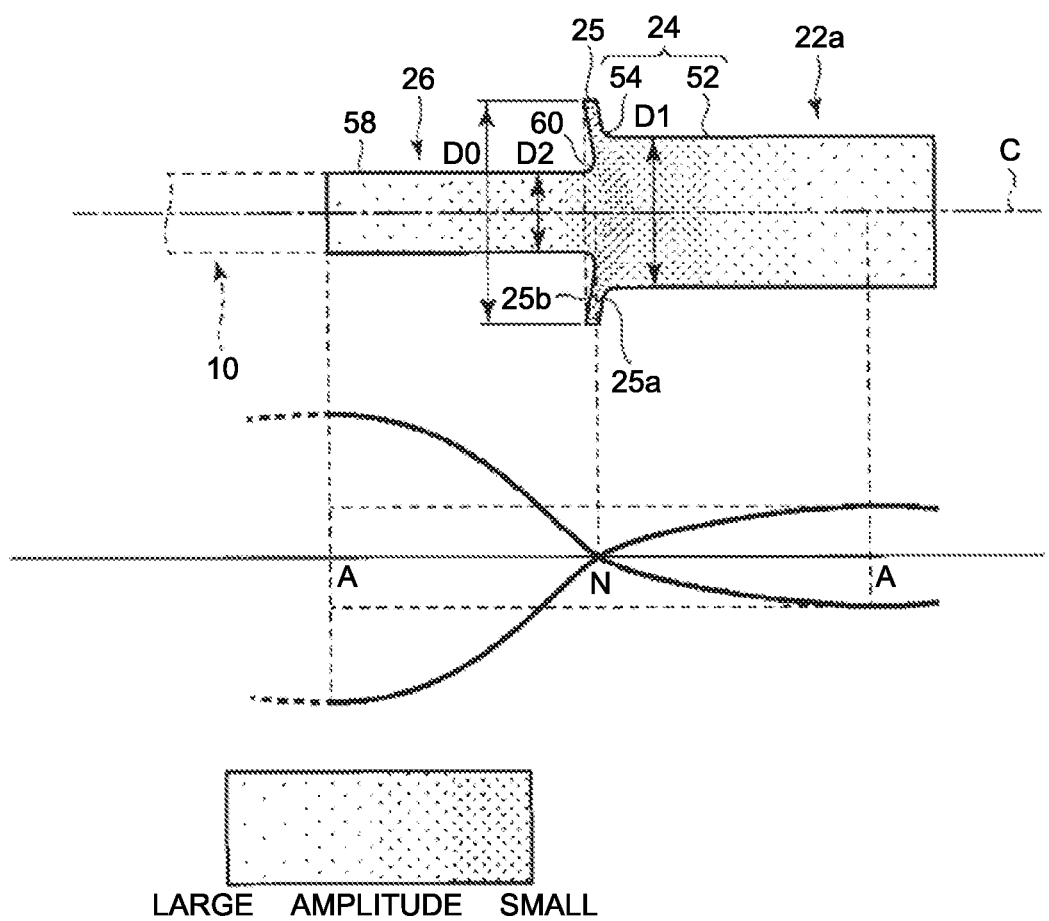
FIG. 3A is a schematic diagram illustrating a vibration transmitter according to a comparative example, and schematically illustrating antinodes, nodes, and amplitude of vibration in a case where the same driving unit as illustrated in FIG. 2A and FIG. 2B generates ultrasonic vibration and inputs longitudinal vibration of the ultrasonic vibration to the vibration transmitter.
Figure 3B:
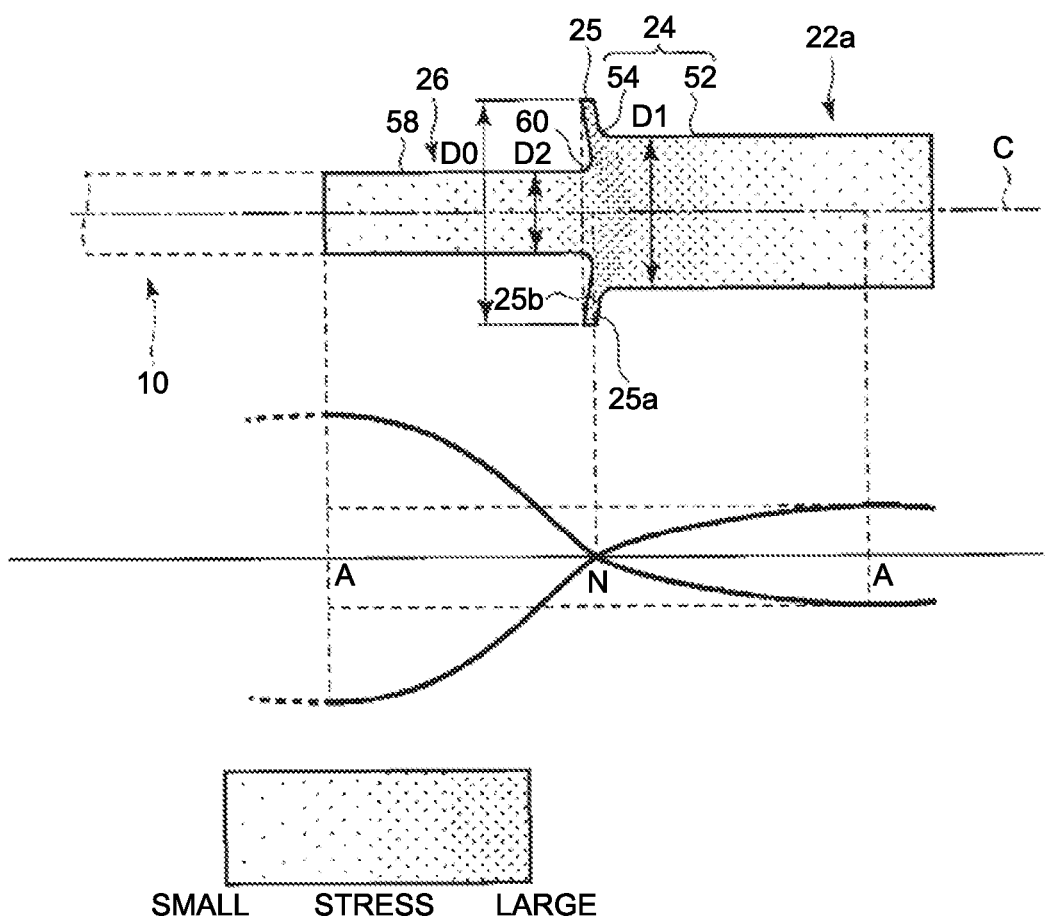
FIG. 3B is a schematic diagram illustrating the vibration transmitter according to the comparative example, and schematically illustrating antinodes, nodes, and amplitude of vibration and a stress distribution in the vibration transmitter in a case where the same driving unit as illustrated in FIG. 2A and FIG. 2B generates ultrasonic vibration and inputs longitudinal vibration of the ultrasonic vibration to the vibration transmitter.

FIG. 3A and FIG. 3B illustrate, as a comparative example of the above embodiment, an example of a vibration transmitter 22a having a different shape from the shape illustrated in FIG. 2A and FIG. 2B. An upper figure in FIG. 3A illustrates a state in which the distal end of the distal end extending portion 58 of the second vibrating unit 26 of the vibration transmitter 22a is displaced on the most proximal end side along the central axis C. A portion with high dot density in the upper figure of FIG. 3A indicates that an absolute value of amplitude is small, and the absolute value of the amplitude increases with a decrease in the density. Dots in the upper figure of FIG. 3B indicate a stress distribution of the vibration transmitter 22a in the state in which the distal end of the distal end extending portion 58 of the second vibrating unit 26 is displaced on the most proximal end side along the central axis C. A portion with high dot density in FIG. 3B indicates that an absolute value of a stress is large, and the absolute value of the stress is reduced with a decrease in the density.

In the vibration transmitter 22a in the upper figures of FIG. 3A and FIG. 3B, a portion near the distal end surface 25b of the supported portion 25 has a different shape from that of the vibration transmitter 22 illustrated in the upper figures of FIG. 2A and FIG. 2B. Lower figures FIG. 3A and FIG. 3B illustrate amplitude of vibration at each position of the vibration transmitter 22 along the central axis C and positions of the antinodes A and the nodes N of the vibration in a case where the same longitudinal vibration as the longitudinal vibration of the ultrasonic vibration of the ultrasonic vibrator 30 of the above embodiment is input to the vibration transmitter 22a. The amplitudes in the lower figures of FIG. 3A and FIG. 3B are schematically illustrated, and, in reality, vibration occurs along the central axis C, so that the amplitude is displaced along the central axis C. Further, while the vibration is being transmitted to the vibration transmitter 22a, the amplitude becomes minimum and the stress and the distortion become maximum at the positions corresponding to the nodes N of the vibration, and the amplitude becomes maximum and the stress and the distortion become minimum at the position corresponding to the antinodes A of the vibration.

As described above, while the vibration is being transmitted to the vibration transmitter 22, the stress (distortion) is distributed as illustrated in the upper figure of FIG. 2B. In the comparative example, as illustrated in the upper figure of FIG. 3B, when a load that causes the proximal end of the second vibrating unit 26 to move to the proximal end side relative to the distal end surface 25b of the supported portion 25 is applied due to the amplitude at the antinode A of vibration on the distal end of the vibration transmitter 22a, the supported portion 25 falls down to the distal end side. Therefore, the supported portion 25 illustrated in FIG. 3A and FIG. 3B are displaced due to input of the vibration to the vibration transmitter 22a.

In the embodiment illustrated in the upper figures of FIG. 2A and FIG. 2B, the thickness of the distal end surface 25b side of the supported portion 25 at the positions distant from the central axis C is increased along the central axis C, relative to the proximal end surface 25a. Therefore, the rigidity of the distal end region of the supported portion 25 at the positions distant from the central axis C in the radial direction is adjusted, i.e., the stress distribution in the distal end region and the stress distribution in the proximal end region at the positions distant from the central axis C in the radial direction are adjusted to be balanced (cancelled out) with respect to the supported portion 25. Therefore, the proximal end of the second vibrating unit 26 can counteract against a load that causes movement toward the proximal end side relative to the distal end surface 25*b* of the supported portion 25. By constructing the portions near the supported portion 25 of the vibration transmitter 22 according to the embodiment described above, it is possible to prevent occurrence of moments, i.e., occurrence of displacement, not only at positions along the central axis C but also at positions distant from the central axis C in the radial direction in the supported portion 25 of the vibration transmitter 22 while the vibration is being transmitted.

As described with respect to the above embodiment, the first relay unit 54 and the second relay unit 56 on the distal end side and the proximal end side of the supported portion 25 of the vibration transmitter 22 have certain shapes by which forces are balanced in a direction along the central axis C. Furthermore, the supported portion 25 has a certain shape by which moments in the supported portion 25 distant from the central axis C in the radial direction in the vibration transmitter 22 are balanced between the distal end side and the proximal end side of the supported portion 25 along the central axis C. Therefore, the vibration transmitter 22 is able to prevent the supported portion 25 from being accidentally displaced while vibration is being transmitted to the vibration transmitter 22. Therefore, it is possible to provide the vibration transmitter 22, the ultrasonic transducer structure 20, and the medical device 40 capable of preventing displacement of the supported portion 25 when the longitudinal vibration of the ultrasonic vibration generated by the ultrasonic vibrator 30 is transmitted along the central axis C. Consequently, for example, it is possible to prevent a user who uses the ultrasonic treatment tool 2 by holding the housing 5 from getting annoyed via the transducer housing 18 that supports the supported portion 25 due to occurrence of displacement of the supported portion 25. Furthermore, by preventing occurrence of displacement of the supported portion 25, it is possible to prevent the supported portion 25 from generating heat.

Moreover, in some embodiments, the energy output source 15 outputs electrical energy that is different from electrical energy supplied to the ultrasonic vibrator 30. For example, electrical energy different from the electrical energy supplied to the ultrasonic vibrator 30 is supplied to each of the rod protruding portion 11 and the jaw 12. Accordingly, a high-frequency electric current flows into a treatment target that is held between the jaw 12 and the rod protruding portion 11.

Upper figures in FIG. 4A and FIG. 4B illustrate another exemplary ultrasonic transducer structure 20. In this example, similarly to the second relay unit 56, the first relay unit 54 is used as a horn that expands amplitude that is output from the distal end of the distal end extending portion 58 of the second vibrating unit 26 with respect to the maximum amplitude at the antinode A of the vibration in the first vibrating unit 24. By constructing the first relay unit 54 as the horn as described above, it becomes possible to increase the amplitude at the antinode A of the vibration on the distal end of the second vibrating unit 26, relative to the amplitude at the antinode A of vibration in the first vibrating unit 24.

The upper figure in FIG. 4A illustrates a state in which the distal end of the distal end extending portion 58 of the second vibrating unit 26 is displaced on the most proximal end side along the central axis C. A portion with high dot density in the upper figure of FIG. 4A indicates that an absolute value of the amplitude is small, and the absolute value of the amplitude increases with a decrease in the density. Similarly to the upper figure in FIG. 4A, an upper figure in FIG. 4B illustrates a state in which the distal end of the distal end extending portion 58 of the second vibrating unit 26 is displaced on the most proximal end side along the central axis C. Dots in the upper figure of FIG. 4B indicate a stress distribution of the vibration transmitter 22 in the state in which the distal end of the distal end extending portion 58 of the second vibrating unit 26 is displaced on the most proximal end side along the central axis C. A portion with high dot density in FIG. 4B indicates that an absolute value of the stress is large, and the absolute value of the stress is reduced with a decrease in the density.

The first relay unit 54 is constructed as a horn that expands amplitude at the position of the antinode A of the vibration. The first relay unit 54 is constructed as the horn in a continuous manner on the proximal end side of the supported portion 25. While the ultrasonic vibration is being transmitted from the ultrasonic vibrator 30, displacement along the central axis C is reduced from the position of the proximal end of the first relay unit 54 toward the supported portion 25, i.e., toward the position of the node N of the vibration. Therefore, a sound speed is apparently reduced from the position of the proximal end of the first relay unit 54 toward the supported portion 25. The first relay unit 54 is constructed as the horn, and an absolute value of the sound speed of the first relay unit 54 is larger than an absolute value of a sound speed at a symmetric position on the proximal end side with respect to the position of the antinode A of the vibration. Here, the sound speed from the position of the antinode A of the vibration on the proximal end side of the supported portion 25 to the position of the node N of the vibration in the supported portion 25 along the central axis C is constant. Because the sound speed is reduced from the position of the proximal end of the first relay unit 54 toward the supported portion 25, a distance from the position of the proximal end of the first relay unit 54 toward the supported portion 25 along the central axis C is reduced to maintain the sound speed constant from the position of the antinode A of the vibration on the proximal end side of the supported portion 25 to the position of the node N of the vibration in the supported portion 25 along the central axis C.

To cope with this, by constructing the first relay unit 54 as the horn, it is possible to increase the amplitude output from the distal end of the vibration transmitter 22, and reduce a length of a region disposed in the transducer housing 18. In other words, a total length of the first relay unit 54 and the proximal end extending portion 52 is reduced as compared to a case in which the first relay unit 54 does not include the horn.

Meanwhile, when the second relay unit 56 is constructed as the horn, a sound speed increases from the position of the supported portion 25, i.e., the position of the node N of the vibration, toward the position of the antinode A of the vibration on the distal end of the second vibrating unit 26. Therefore, it is preferable to increase a distance between the supported portion 25 and the distal end of the second vibrating unit 56 in accordance with the sound speed.

In the examples illustrated in FIG. 4A and FIG. 4B, due to the amplitude at the position of the antinode A of the vibration on the distal end of the distal end extending portion 58 in the vibration transmitter 22, a load that causes movement toward the proximal end side relative to the distal end surface 25b of the supported portion 25 is applied to the proximal end of the second vibrating unit 26. At the position of the node N of the vibration inside the supported portion 25, the sum of forces is balanced along the central axis C.

As for the stress distribution in the supported portion 25 in FIG. 4B, stress distributions on the distal end side and the proximal end side of the supported portion 25 along the central axis C are substantially the same in the supported portion 25 distant from the central axis C in the radial direction and in the vicinity of the supported portion 25. The first relay unit 54 and the second relay unit 56 of the vibration transmitter 22 according to the above embodiment have certain shapes by which, while the longitudinal vibration of the ultrasonic vibration is being input to the vibration transmitter 22, the stress distribution in the first relay unit 54 connected to the proximal end side of the supported portion 25 and the stress distribution in the second relay unit 56 connected to the distal end side of the supported portion 25 are, at positions distant from the central axis C in the radial direction, balanced with respect to the supported portion 25 along the central axis C. In other words, moments near the proximal end surface 25a and the distal end surface 25b of the supported portion 25 distant from the central axis C in the radial direction are cancelled out due to the principle of superposition. Therefore, the stress distribution of the supported portion 25 in the upper figure of FIG. 4B indicates that it is possible to, at positions distant from the central axis C in the radial direction, counteract against a load that is applied when the distal end of the distal end extending portion 58 of the second vibrating unit 26 is displaced on the most proximal end side along the central axis C. Therefore, the first relay unit 54, the supported portion 25, and the second relay unit 56 of the vibration transmitter 22 have certain shapes that prevent occurrence of moments in the supported portion 25.

Meanwhile, the rigidity near the boundary between the distal end surface 25b of the supported portion 25 and the proximal end of the second relay unit 56 is larger than the rigidity near the boundary between the proximal end surface 25a of the supported portion 25 and the distal end of the first relay unit 54. Therefore, in the examples illustrated in the upper figures of FIG. 4A and FIG. 4B, it is possible to prevent occurrence of moments in the supported portion 25 that may cause the supported portion 25 to move to the distal end side along the central axis C against the load that is applied when the distal end of the distal end extending portion 58 of the second vibrating unit 26 is displaced on the most distal end side along the central axis C.

Therefore, the supported portion 25 has a certain shape by which moments in the supported portion 25 distant from the central axis C in the radial direction in the vibration transmitter 22 are balanced between the distal end side and the proximal end side of the supported portion 25 along the central axis C. Therefore, it is possible to provide the vibration transmitter 22, the ultrasonic transducer structure 20, and the medical device 40 capable of preventing displacement of the supported portion 25 when the longitudinal vibration of the ultrasonic vibration generated by the ultrasonic vibrator 30 is transmitted along the central axis C. Consequently, for example, it is possible to prevent a user who uses the ultrasonic treatment tool 2 by holding the housing 5 from getting annoyed via the transducer housing 18 that supports the supported portion 25 due to occurrence of displacement of the supported portion 25.

Another exemplary embodiment will be described below with reference to FIG. 5A and FIG. 5B. The same components and components having the same functions as those described in the above embodiment are denoted by the same reference symbols, and detailed explanation thereof will be omitted.

Upper figures in FIG. 5A and FIG. 5B illustrate the ultrasonic transducer structure 20. The upper figure in FIG. 5A illustrates a state in which the distal end of the distal end extending portion 58 of the second vibrating unit 26 is displaced on the most proximal end side along the central axis C. A portion with high dot density in the upper figure of FIG. 5A indicates that an absolute value of the amplitude is small, and the absolute value of the amplitude increases with a decrease in the density. Similarly to the upper figure in FIG. 5A, the upper figure in FIG. 5B illustrates a state in which the distal end of the distal end extending portion 58 of the second vibrating unit 26 is displaced on the most proximal end side along the central axis C. Dots in the upper figure of FIG. 5B indicate a stress distribution of the vibration transmitter 22 in the state in which the distal end of the distal end extending portion 58 of the second vibrating unit 26 is displaced on the most proximal end side along the central axis C. A portion with high dot density in FIG. 5B indicates that an absolute value of the stress is large, and the absolute value of the stress is reduced with a decrease in the density.

In this embodiment, an example will be described in which the first relay unit 54 and the second relay unit 56 connected to the supported portion 25 are symmetric or approximately symmetric with respect to the supported portion 25.

In the proximal end surface 25a of the supported portion 25, a boundary with the distal end of the first relay unit 54 is formed. In the distal end surface 25b of the supported portion 25, a boundary with the proximal end of the second relay unit 56 is formed. The outer diameter D1 at the boundary between the proximal end surface 25a of the supported portion 25 and the distal end of the first relay unit 54 is the same or approximately the same as the outer diameter D2 at the boundary between the distal end surface 25b of the supported portion 25 and the proximal end of the second relay unit 56.

Furthermore, a state of change in a cross-sectional area of a region within a range of a length L1 from the proximal end surface 25a of the supported portion 25 to the proximal end side along the central axis C in the first relay unit 54 and a state of change in a cross-sectional area of a region within a range of a length L2 (=L1) from the distal end surface 25b of the supported portion 25 to the distal end side in the second relay unit 56 are symmetric or approximately symmetric with respect to the supported portion 25.

Here, the region corresponding to the length L1 from the proximal end surface 25a of the supported portion 25 to the proximal end side in the first relay unit 54 is referred to as a first region 64. The region corresponding to the length L2 from the distal end surface 25b of the supported portion 25 to the distal end side in the second relay unit 56 is referred to as a second region 66. An adjustment unit 67 that adjusts a balance of rigidity with respect to the first relay unit 54 on the proximal end side of the supported portion 25 is provided on the distal end side of the second region 66. A horn 67a is provided on the distal end side of the adjustment unit 67.

In the example illustrated in the upper figures of FIG. 5A and FIG. 5B, in the vicinity of the supported portion 25, the first region 64 of the first relay unit 54 is displaced in the distal end direction C2 of the vibration transmitter 22, and the second region 66 of the second relay unit 56 is displaced in the proximal end direction C1 of the vibration transmitter 22. In this case, the sum of forces is balanced along the central axis C at the position of the node N of the vibration inside the supported portion 25.

As illustrated in the upper figure of FIG. 5B, due to the second region 66, the outer diameter D2 at a certain distance L2 on the distal end side of the supported portion 25 becomes the same as the outer diameter D1 at a certain distance L1 (=L2) from the supported portion 25 to the proximal end side within the first region 64. In other words, the supported portion 25 adjusts, in cooperation with the first region 64 and the second region 66, rigidities of the regions connected to the proximal end surface 25a and the distal end surface 25b of the supported portion 25 at positions distant from the central axis C to be approximately the same. Furthermore, the second relay unit 56 adjusts the rigidity thereof to be approximately the same as the rigidity of the first relay unit 54, with the aid of the adjustment unit 67 as described above.

Amplitude at the position of the antinode A of vibration on the distal end of the distal end extending portion 58 of the vibration transmitter 22 is larger than amplitude at the position of the antinode A of vibration in the first vibrating unit 24. Therefore, a load that causes movement toward the proximal end side relative to the distal end surface 25b of the supported portion 25 is applied to the proximal end of the second vibrating unit 26. In the vicinity of the node N of the vibration in FIG. 5B, stresses are applied in opposite directions along the central axis C. In FIG. 5B, in the supported portion 25 distant from the central axis C in the radial direction and in the vicinity of the supported portion 25, stress distributions are substantially the same between the distal end side and the proximal end side of the supported portion 25 along the central axis C. The first relay unit 54 and the second relay unit 56 of the vibration transmitter 22 according to this embodiment have certain shapes by which, while the longitudinal vibration of the ultrasonic vibration is being input to the vibration transmitter 22, the stress distribution in the first relay unit 54 connected to the proximal end side of the supported portion 25 and the stress distribution in the second relay unit 56 connected to the distal end side are, at positions distant from the central axis C in the radial direction, balanced with respect to the supported portion 25 along the central axis C. In other words, moments near the proximal end surface 25a and the distal end surface 25b of the supported portion 25 distant from the central axis C in the radial direction are cancelled out due to the principle of superposition. Therefore, the stress distribution of the supported portion 25 in the upper figure in FIG. 5B indicate that it is possible to, at positions distant from the central axis C in the radial direction, counteract against a load that is applied when the distal end of the distal end extending portion 58 of the second vibrating unit 26 is displaced on the most proximal end side along the central axis C. Therefore, the first relay unit 54, the supported portion 25, and the second relay unit 56 of the vibration transmitter 22 according to this embodiment have certain shapes that prevent occurrence of moments in the supported portion 25.

Meanwhile, the rigidity of the second relay unit 56 on the distal end side of the supported portion 25 is adjusted to be approximately the same as the rigidity of the first relay unit 54 on the proximal end side of the supported portion 25 with the aid of the adjustment unit 67. Therefore, in the examples illustrated in FIG. 5A and FIG. 5B, it is possible to prevent occurrence of moments in the supported portion 25 that may cause the supported portion 25 to move to the distal end side along the central axis C against the load that is applied when the distal end of the distal end extending portion 58 of the second vibrating unit 26 is displaced on the most distal end side along the central axis C.

As described above, according to this embodiment, the first relay unit 54 and the second relay unit 56 on the distal end side and the proximal end side of the supported portion 25 in the vibration transmitter 22 have certain shapes by which forces in a direction along the central axis C are balanced. Furthermore, the supported portion 25 has a certain shape by which moments in the supported portion 25 distant from the central axis C in the radial direction in the vibration transmitter 22 are balanced between the distal end side and the proximal end side of the supported portion 25 along the central axis C. Therefore, the vibration transmitter 22 is able to prevent the supported portion 25 from being displaced accidentally displaced while vibration is being transmitted to the vibration transmitter 22. Therefore, it is possible to provide the vibration transmitter 22, the ultrasonic transducer structure 20, and the medical device 40 capable of preventing displacement of the supported portion 25 when the longitudinal vibration of the ultrasonic vibration generated by the ultrasonic vibrator 30 is transmitted along the central axis C. Consequently, for example, it is possible to prevent a user who uses the ultrasonic treatment tool 2 by holding the housing 5 from getting annoyed via the transducer housing 18 that supports the supported portion 25 due to occurrence of displacement of the supported portion 25. Furthermore, by preventing occurrence of displacement of the supported portion 25, it is possible to prevent the supported portion 25 from generating heat.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibration transmitter comprising:
   a proximal end extending portion that extends along a central axis from a proximal end to a distal end, and is configured to receive longitudinal vibration of ultrasonic vibration generated by an ultrasonic vibrator fixed to the proximal end;
   a supported portion that: (i) is provided on a distal end portion of the proximal end extending portion along the central axis, (ii) located on an outer periphery of a node of vibration on the central axis or on an outer periphery near the node of the vibration while the longitudinal vibration is being transmitted along the central axis, (iii) protrudes outward in a radial direction orthogonal to the central axis, and (iv) is supported by a housing;
   a distal end extending portion that: (i) is disposed on a distal end portion of the supported portion along the central axis, (ii) is configured to receive the longitudinal vibration, and (iii) has an outer diameter smaller than an outer diameter of the supported portion;
   a first relay provided between the supported portion and the proximal end extending portion; and
   a second relay provided between the supported portion and the distal end extending portion, wherein:
   the second relay includes a horn that having an outer diameter at a position continuously adjacent to the supported portion that is larger than:
      an outer diameter of the first relay at a position continuously adjacent to the supported portion, and the outer diameter of the distal end extending portion;
the horn is configured to expand an amplitude of vibration output from a distal end of the distal end extending portion to be larger than a maximum amplitude at an antinode of vibration in the first relay or the proximal end extending portion while the longitudinal vibration is being transmitted; and
wherein the first relay and the second relay are shaped such that, while the longitudinal vibration is being propagated to the vibration transmitter:
  a displacement distribution of the first relay and a displacement distribution of the second relay at positions distant from the central axis in the radial direction are balanced with respect to the supported portion, and
  displacement of the supported portion in a direction along the central axis is prevented.

2. The vibration transmitter according to claim 1, wherein a boundary between the second relay and the support portion has a cross-sectional area perpendicular to the central axis that is larger than a cross-sectional area perpendicular to the central axis at a boundary between the first relay and the supported portion.

3. The vibration transmitter according to claim 1, wherein the first relay and the second relay are shaped such that, while the longitudinal vibration is being propagated to the vibration transmitter:
  a stress distribution in the first relay and a stress distribution in the second relay at positions distant from the central axis in the radial direction are balanced with respect to the supported portion, and
  vibration due to occurrence of moments in the supported portion at the positions distant from the central axis in the radial direction is prevented.

4. The vibration transmitter according to claim 1, wherein the first relay and the second relay have certain shapes that are symmetric or approximately symmetric with respect to the supported portion along the central axis, and by which, while the longitudinal vibration is being propagated to the vibration transmitter, vibration due to occurrence of moments in the supported portion distant from the central axis in the radial direction is prevented and displacement of the supported portion in a direction along the central axis is prevented.

5. The vibration transmitter according to claim 1, wherein the first relay includes a horn that is connected to the supported portion and is configured to expand the amplitude of vibration output from the distal end of the distal end extending portion to be larger than the maximum amplitude at the antinode of the vibration in the first relay or the proximal end extending portion while the longitudinal vibration is being transmitted.

6. The vibration transmitter according to claim 5, wherein a total length of the first relay and the proximal end extending portion is reduced as compared to a case in which the first relay does not include the horn.

7. The vibration transmitter according to claim 1, wherein the distal end extending portion includes, at the distal end thereof, a connecting portion to which a treatment vibration transmitter having a treatment portion that is connectable on the distal end portion along the central axis.

8. The vibration transmitter according to claim 1, wherein the supported portion has a plate shape that protrudes outward in the radial direction with respect to the central axis.

9. The vibration transmitter according to claim 8, wherein the supported portion has a disk shape.

10. An ultrasonic transducer structure comprising:
the vibration transmitter according to claim 1;
wherein the ultrasonic vibrator is fixed to a proximal end of the vibration transmitter, and configured to generate the longitudinal vibration upon receiving energy; and
a pressing body that holds the ultrasonic vibrator in a space between the pressing body and the proximal end of the vibration transmitter, and presses the ultrasonic vibrator toward the proximal end of the vibration transmitter.

11. A medical device comprising:
the ultrasonic transducer structure according to claim 10; and
wherein the housing houses the ultrasonic transducer structure and supports the supported portion, the housing having an electrical insulation property.

12. The medical device according to claim 11, wherein a boundary between the second relay and the support portion has a cross-sectional area perpendicular to the central axis that is larger than a cross-sectional area perpendicular to the central axis at a boundary between the first relay and the supported portion.

13. The medical device according to claim 11, wherein the first relay and the second relay are shaped such that, while the longitudinal vibration is being propagated to the vibration transmitter:
  a stress distribution in the first relay and a stress distribution in the second relay at positions distant from the central axis in the radial direction are balanced with respect to the supported portion, and
  vibration due to occurrence of moments in the supported portion at the positions distant from the central axis in the radial direction is prevented.

14. The medical device according to claim 11, wherein the first relay and the second relay have certain shapes that are symmetric or approximately symmetric with respect to the supported portion along the central axis, and by which, while the longitudinal vibration is being propagated to the vibration transmitter, vibration due to occurrence of moments in the supported portion distant from the central axis in the radial direction is prevented and displacement of the supported portion in a direction along the central axis is prevented.

15. The medical device according to claim 11, wherein the first relay includes a horn that is connected to the supported portion and is configured to expand the amplitude of vibration output from the distal end of the distal end extending portion to be larger than the maximum amplitude at the antinode of the vibration in the first relay or the proximal end extending portion while the longitudinal vibration is being transmitted.

16. The medical device according to claim 15, wherein a total length of the first relay and the proximal end extending portion is reduced as compared to a case in which the first relay does not include the horn.

17. The medical device according to claim 11, wherein the distal end extending portion includes, at the distal end thereof, a connecting portion to which a treatment vibration transmitter having a treatment portion is connectable on the distal end portion along the central axis.

18. A vibration transmitter comprising:
a proximal end extending portion that extends along a central axis from a proximal end to a distal end, and is configured to receive longitudinal vibration of ultrasonic vibration generated by an ultrasonic vibrator fixed to the proximal end;

a supported portion that: (i) is provided on a distal end portion of the proximal end extending portion along the central axis, (ii) located on an outer periphery of a node of vibration on the central axis or on an outer periphery near the node of the vibration while the longitudinal vibration is being transmitted along the central axis, (iii) protrudes outward in a radial direction orthogonal to the central axis, and (iv) is supported by a housing;

a distal end extending portion that: (i) is disposed on a distal end portion of the supported portion along the central axis, (ii) is configured to receive the longitudinal vibration, and (iii) has an outer diameter smaller than an outer diameter of the supported portion;

a first relay provided between the supported portion and the proximal end extending portion; and a second relay provided between the supported portion and the distal end extending portion, the first relay and the second relay being shaped such that, while the longitudinal vibration of the ultrasonic vibration is being propagated:

stress distributions in the first relay and second relay at positions distant from the central axis in the radial direction become symmetric with respect to the supported portion along the central axis, and an occurrence of moments in the supported portion is prevented to thereby prevent vibration of the supported portion.

* * * * *